US009442048B2

(12) United States Patent
Durbin et al.

(10) Patent No.: US 9,442,048 B2
(45) Date of Patent: Sep. 13, 2016

(54) GAS SENSING SYSTEM AND METHOD

(71) Applicant: The Boeing Company, Chicago, IL (US)

(72) Inventors: Richard R. Durbin, Mukilteo, WA (US); Jeffrey W. Glasnovich, Bothell, WA (US)

(73) Assignee: The Boeing Company, Chicago, IL (US)

( * ) Notice: Subject to any disclaimer, the term of this patent is extended or adjusted under 35 U.S.C. 154(b) by 301 days.

(21) Appl. No.: 14/044,494

(22) Filed: Oct. 2, 2013

(65) Prior Publication Data
US 2015/0090001 A1 Apr. 2, 2015

(51) Int. Cl.
*G01N 1/26* (2006.01)
*G01N 33/00* (2006.01)
*G01N 1/22* (2006.01)

(52) U.S. Cl.
CPC ............... *G01N 1/26* (2013.01); *G01N 1/2273* (2013.01); *G01N 33/0022* (2013.01)

(58) Field of Classification Search
CPC ...................................................... G01N 1/26
See application file for complete search history.

(56) References Cited

U.S. PATENT DOCUMENTS

| 4,345,610 | A | 8/1982 | Herter et al. | |
|---|---|---|---|---|
| 5,293,771 | A * | 3/1994 | Ridenour | G01M 3/20 340/605 |
| 6,125,710 | A * | 10/2000 | Sharp | G01N 1/26 73/863.01 |
| 6,241,950 | B1 * | 6/2001 | Veelenturf | G01N 1/26 422/537 |
| 7,216,556 | B2 * | 5/2007 | Desrochers | G01N 1/22 73/863.01 |
| 7,360,461 | B2 * | 4/2008 | Desrochers | G01N 1/22 73/863.71 |
| 7,415,901 | B2 * | 8/2008 | Desrochers | G01N 1/26 236/1 B |
| 2006/0234621 | A1 * | 10/2006 | Desrochers | F24F 3/044 454/239 |
| 2011/0308453 | A1 | 12/2011 | Su et al. | |
| 2014/0260692 | A1 * | 9/2014 | Sharp | G01N 1/2273 73/863.23 |

FOREIGN PATENT DOCUMENTS

GB 2239952 A 7/1991

OTHER PUBLICATIONS

Kawai, Kentaro, et al., Multiplexed Pneumatic Valve Control System for Large Scale Integrated Microfluidic Circuit (LSIMC), Twelfth International Conference on Miniaturized Systems for Chemistry and Life Sciences, Oct. 12-16, 2008, San Diego, CA.
Extended European Search Report dated Feb. 4, 2015; European Patent Office, Application No. 14181818.7-1559; Reference No. E/2QK78/1233, The Boeing Company, 8 pages.
Canadian Office Action dated Oct. 16, 2015; Application No. 2,857,822; Canadian Intellectual Property Office, 4 pages.

* cited by examiner

*Primary Examiner* — Peter Macchiarolo
*Assistant Examiner* — Nathaniel Kolb
(74) *Attorney, Agent, or Firm* — Toler Law Group, PC

(57) ABSTRACT

Systems and methods for sensing gas are disclosed. In one aspect, a system to monitor an output of a gas source comprises a chamber comprising a plurality of input ports to receive inputs from a plurality of gas sources, and means for repeatedly blocking one of the plurality of input ports for a period of time, detecting which one of the plurality of input ports is blocked, collecting data from a plurality of samples from the enclosure while the one of the plurality of input ports is blocked, and storing the data in a memory in association with an indicator of which one of the plurality of input ports is blocked. Other embodiments may be described.

16 Claims, 4 Drawing Sheets

GAS SENSING SYSTEM AND METHOD

BACKGROUND

The subject matter described herein relates to gas sensor systems for monitoring of gases.

In various applications it may be useful to monitor attributes of one gas source in a plurality of gas sources. For example, some aircraft include an air separation unit (ASU) which has a plurality of air separation modules (ASMs). The ASMs supply an inert gas such as nitrogen to a fuel tank to maintain inerting in the tank as fuel is consumed by the aircraft. The inert gas may also be supplied to systems other than fuel tanks.

Existing measurement systems route the output of ASMs through a gas sensor to determine the relative amounts of gas in the output flow of the ASMs. For example, the amount of oxygen in the combined output flow may be measured. If the amount of oxygen in the combined output exceeds a predetermined threshold, then it is possible that all the ASMs may be, repaired, or replaced, even though only one of the ASMs require servicing. Accordingly, systems and methods to sense gas from a single gas source in a multi-source system may find utility.

SUMMARY

In one aspect, a system to monitor an output of a gas source comprises a chamber comprising a plurality of input ports to receive inputs from a plurality of gas sources, and means for repeatedly blocking one of the plurality of input ports for a period of time, detecting which one of the plurality of input ports is blocked, collecting data from a plurality of samples from the enclosure while the one of the plurality of input ports is blocked, and storing the data in a memory in association with an indicator of which one of the plurality of input ports is blocked.

In another aspect, an aircraft comprises a fuselage and a system to monitor an output of a gas source comprises a chamber comprising a plurality of input ports to receive inputs from a plurality of gas sources, and means for repeatedly blocking one of the plurality of input ports for a period of time, detecting which one of the plurality of input ports is blocked, collecting data from a plurality of samples from the enclosure while the one of the plurality of input ports is blocked, and storing the data in a memory in association with an indicator of which one of the plurality of input ports is blocked.

In another aspect, a method to monitor an output of a gas source, comprises receiving inputs from a plurality of gas sources in a plurality of input ports in a chamber, repeatedly blocking one of the plurality of input ports for a period of time, detecting which one of the plurality of input ports is blocked, collecting data from a plurality of samples from the enclosure while the one of the plurality of input ports is blocked, and storing the data in a memory in association with an indicator of which one of the plurality of input ports is blocked.

Further areas of applicability will become apparent from the description provided herein. It should be understood that the description and specific examples are intended for purposes of illustration only and are not intended to limit the scope of the present disclosure

BRIEF DESCRIPTION OF THE DRAWINGS

Embodiments of methods and systems in accordance with the teachings of the present disclosure are described in detail below with reference to the following drawings.

DETAILED DESCRIPTION

Specific details of certain embodiments are set forth in the following description and the associated figures to provide a thorough understanding of such embodiments. One skilled in the art will understand, however, that alternate embodiments may be practiced without several of the details described in the following description.

The invention may be described herein in terms of functional and/or logical block components and various processing steps. For the sake of brevity, conventional techniques related to data transmission, signaling, network control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The following description may refer to components or features being "connected" or "coupled" or "bonded" together. As used herein, unless expressly stated otherwise, "connected" means that one component/feature is in direct physically contact with another component/feature. Likewise, unless expressly stated otherwise, "coupled" or "bonded" means that one component/feature is directly or indirectly joined to (or directly or indirectly communicates with) another component/feature, and not necessarily directly physically connected. Thus, although the figures may depict example arrangements of elements, additional intervening elements, devices, features, or components may be present in an actual embodiment.

Described herein are examples of systems and methods for gas sensing. More particularly, the systems and methods described herein enable the sensing of gas output from a single gas supply source in a multi-source system. In brief, a chamber is provided with a plurality of input ports, each of which receives a gas input from a gas source in a multi-source system. One of the input ports is blocked for a period of time and data is collected from the remaining input sources. The data is stored in association with an indicator of which input port was blocked while the data was collected. This process is then repeated in a pseudo-random fashion to collect a robust data set. A processing device may be used to analyze the data to determine a gas measurement from the input ports, which correspond to the respective gas sources.

Figure 1:
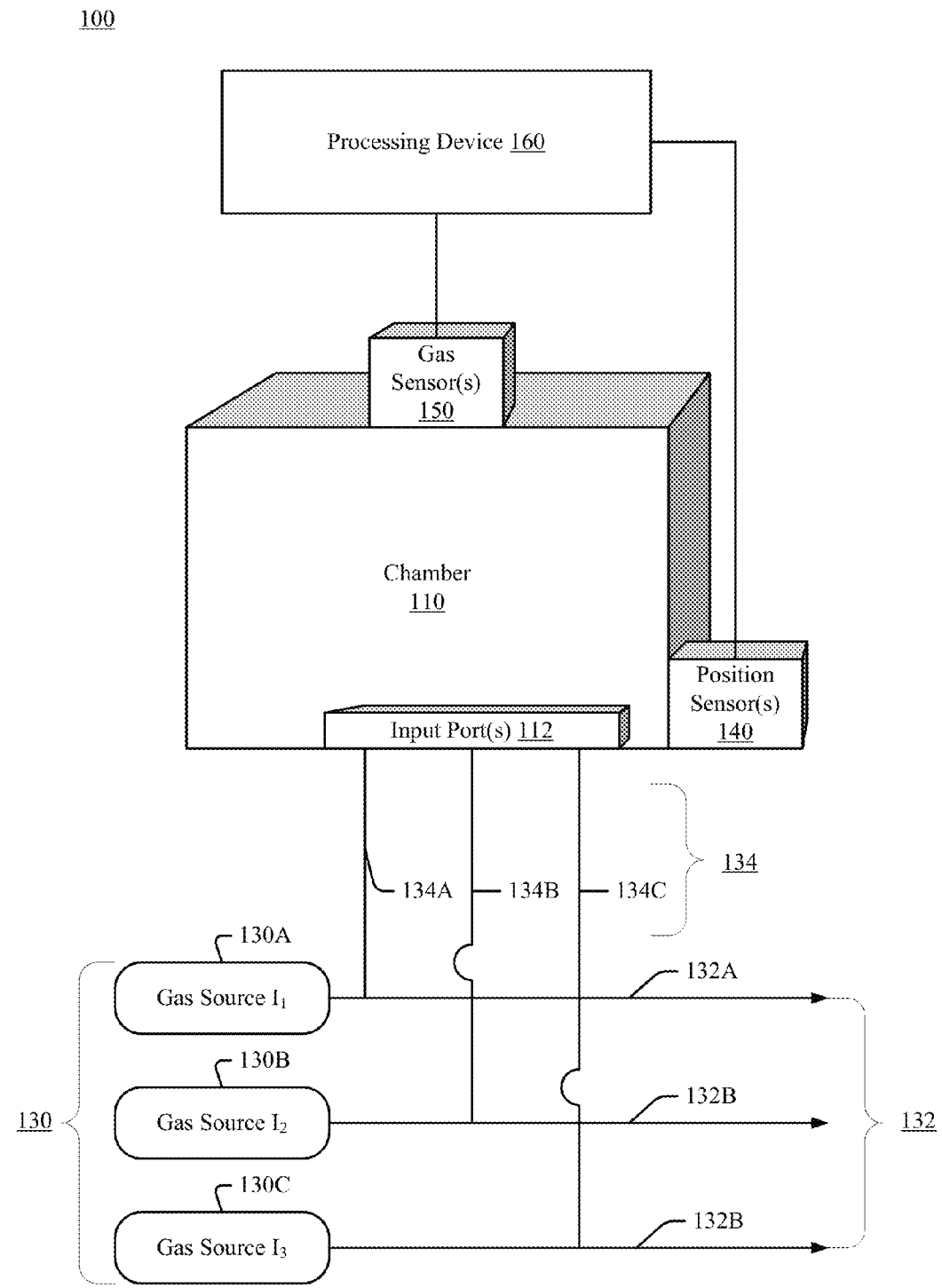
FIG. 1 is a schematic, high-level illustration of a gas sensing system to detect, according to aspects.

FIG. 1 is a schematic, high-level illustration of a gas sensing system according to aspects. Referring to FIG. 1, in some aspects a system to monitor a composition of a gas comprises a chamber 110 which comprises a plurality of input ports 112 configured to received a portion of gas from a plurality of gas sources 130A, 130B, 130C, which may be referred to collectively herein by reference numeral 130.

The particular shape and size of chamber 110 may be determined at least in part by the parameters (e.g., gas flow and pressure) of the gas monitoring system 100. Chamber 110 may include one or more vents to allow gas directed into the chamber 110 via input ports 112 to be vented from the chamber 110.

The specific example system depicted in FIG. 1 includes three gas sources, but it will be understood that other examples may include more or fewer gas sources 130. The gas sources 130 may be coupled to a remote system or device via output lines 132A, 132B, 132C, which may be referred to collectively herein by reference number 132. The output lines 132 comprise respective feed lines 134A, 134B, 134C, which may be referred to collectively herein by reference numeral 134, coupled to input ports 112 of chamber 110. In some examples the system 110 further includes one or more position sensors 140. Additional details of the chamber 110 will be described below with reference to FIGS. 2-4.

System 100 further comprises at least one gas sensor 150 positioned to monitor the gas in chamber 110. The particular type of gas sensor 150 may be a product of the gas or gases that system 100 is monitoring. For example, in the ASM application described above the gas sensor 150 may be an oxygen sensor which may be configured to detect the amount of oxygen in the gas in chamber 110. In other examples the gas sensor 150 may be any of a number of combustible, flammable and toxic gases and vapors such as Carbon Dioxide, Carbon Monoxide, Ozone, Liquefied Petroleum Gas (Propane, Butane, etc.), Combustibles (fuel vapors, etc.) Alcohol, Hydrogen, Smoke, Hydrogen Sulfide, Chlorine, Chlorine Dioxide, Sulfur Dioxide, Nitrogen Dioxide, Ammonia, Hydrogen Chloride, Hydrogen Fluoride, Nitric Oxide, Hydrogen Cyanide, Ethylene Oxide and the like.

System 100 further includes a processing device 160 communicatively coupled to the position sensor(s) 140 and the gas sensor(s) 150. Additional details of the processing device 160 are described with reference to FIG. 5, below.

Figure 2:
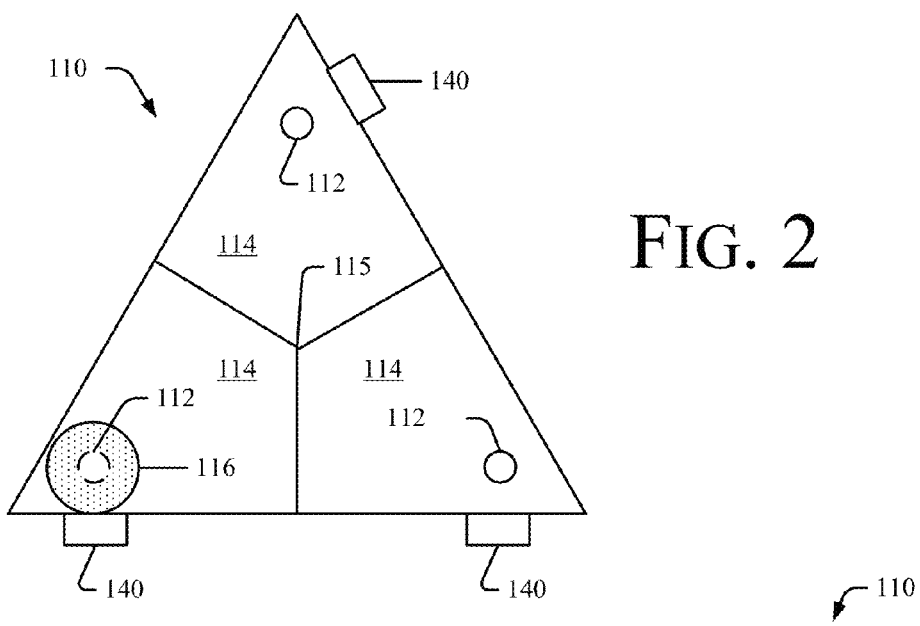
FIGS. 2-4 are schematic top views of chambers which may be used in a gas sensing system, according to aspects.
Figure 3:
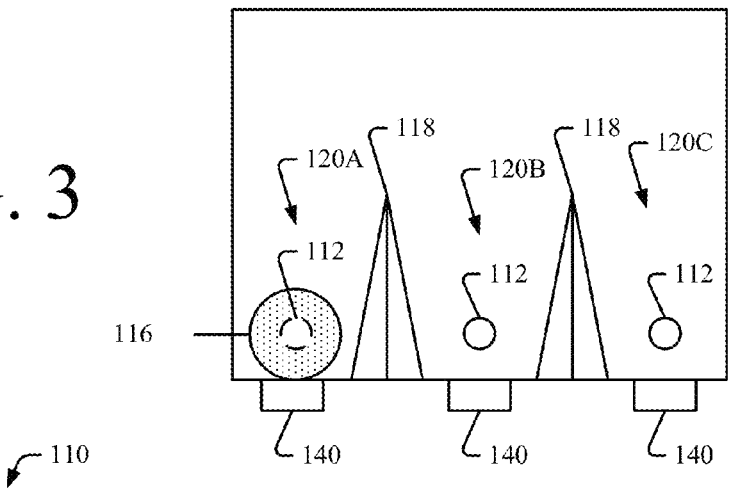
Figure 4:
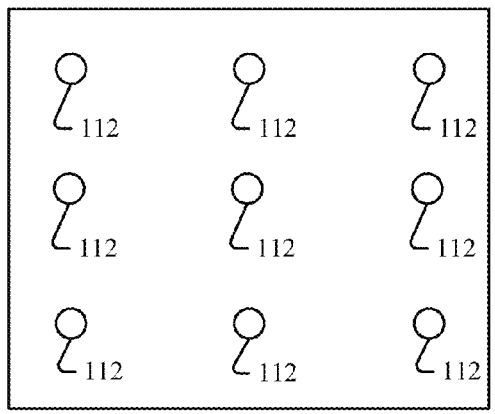

FIGS. 2-4 are schematic top views of chambers 110 which may be used in a gas sensing system, according to aspects. In some examples the chamber 110 may be configured to block, in a pseudo-random fashion, one of the plurality of input ports 112 for a period of time. In the example depicted in FIG. 2 the chamber 110 presents a triangular cross-sectional shape and comprises three sloped surfaces 114 on the floor of the chamber 110 that intersect at a peak 115. The input ports 112 are positioned proximate to the corners, which are the low points, of the respective sloped surfaces 114 of the floor.

A ball 116 is disposed within chamber 110 and able to roll relatively freely on the sloped surfaces 114 of the chamber 110. In some embodiments the ball 116 may comprise a ferrous material, e.g., steel or the like. Position sensors 140 may be positioned proximate the input ports 112 to detect when the ball 116 is positioned over the input port 112. In some examples the position sensors 114 may be embodied as Hall effect sensors.

In operation the chamber of FIG. 2 may be positioned such that the plane established by the three corners of the floor is approximately level (i.e., parallel to the earth) so that the force of gravity tends to pull the ball 116 into a corner of the chamber 110, such that the ball 116 blocks one of the input ports 112. The ball 116 may be moved periodically by subjecting the chamber 110 to acceleration. For example, in a vehicle such as a waterborne vehicle the chamber 110 may be accelerated as a result of motion due to waves or the like. Similarly, in a land-based vehicle chamber 110 may be accelerated as a result of motion due to starting and stopping the vehicle, turning, or hitting bumps on a road. In an airborne vehicle chamber 110 may be accelerated as a result of motion due to taking off, landing, turning, or turbulence. In an example in which the chamber 110 is used in a stationary environment the chamber 110 may be mounted on or coupled to a vibrating element, e.g., a vibrating platform or the like, which may be activated on a periodic basis.

In response to acceleration of the chamber 110 the ball 116 may roll on the sloped surfaces 114, eventually coming to rest under the force of gravity in one of the corners such that ball 116 blocks an input port 112. Thus, the combination of the sloped surfaces 114 and the ball 116 provide a mechanism to block, in a pseudo-random fashion, one of the plurality of input ports 112 in the chamber 110. The position sensor 140 proximate the input port 112 detects that the ball is blocking the input port and, in response thereto, generates a signal which is communicated to processing device 160.

It will be recognized that while the chamber 110 depicted in FIG. 2 has three sloped surfaces 114, in other examples the chamber 110 may be provided with more or fewer sloped surfaces 114. The particular number of sloped surfaces is not critical and may be, at least in part, a function of the number of input ports 112 to be monitored. Further, while a preferred embodiment may include a slopped surface other embodiments may be envisaged such as a flat floor or a floor having sloped surfaces with the input port 112 in a central position with respect to the floor area. Further, other embodiments may include multiple balls or devices to block the input ports.

The example depicted in FIG. 3 uses a technique similar to the example depicted in FIG. 2 to block, in a pseudo-random fashion, one of the plurality of input ports 112 in the chamber 110. Referring to FIG. 3, the chamber 110 comprises a plurality of structures 118 which define a plurality of discrete sections 120A, 120B, 120C, which may be referred to collectively herein by reference numeral 120. The input ports 112 are positioned in the respective sections 120, and the floor of the chamber 110 may be sloped such that the input ports 112 are at the low point of the chamber.

As described above, the ball 116 may be moved due to acceleration and will settle, under the force of gravity, back into one of the sections 120, thereby blocking, in a pseudo-random fashion, one of the plurality of input ports 112 for a period of time. The position sensor 140 proximate the input port 112 detects that the ball 116 is blocking the input port 112 and, in response thereto, generates a signal which is communicated to processing device 160.

It will be recognized that while the chamber 110 depicted in FIG. 3 has two structures 118 which define three sections 120, in other examples the chamber 110 may be provided with more or fewer structures 118 defining more or fewer sections 120. The particular number of sections 120 is not critical and may be, at least in part, a function of the number of input ports 112 to be monitored.

In the example depicted in FIG. 4 the chamber 110 may comprise a plurality of input ports 112 which can be selectively opened and closed by a valve or regulator which may be controlled by a remote device such as processing device 160. For example, processing device 160 may comprise logic to selectively close one of the input ports 112 in either a pseudo-random or an ordered fashion. The input port 112 may remain closed for a predetermined period of time, which may also be determined in a pseudo-random fashion. For example, the processing device 160 may utilize a random number generator to select an input port 112 to close and to select a period of time to keep the port closed or use a predetermined time value. After the time period elapses the processing device may utilize the random number generator or a predetermined sequence to close another input port. The example depicted in FIG. 4 does not require position sensor(s) 140 because the processing device 160 selects the input port 112 to close.

Figure 5:
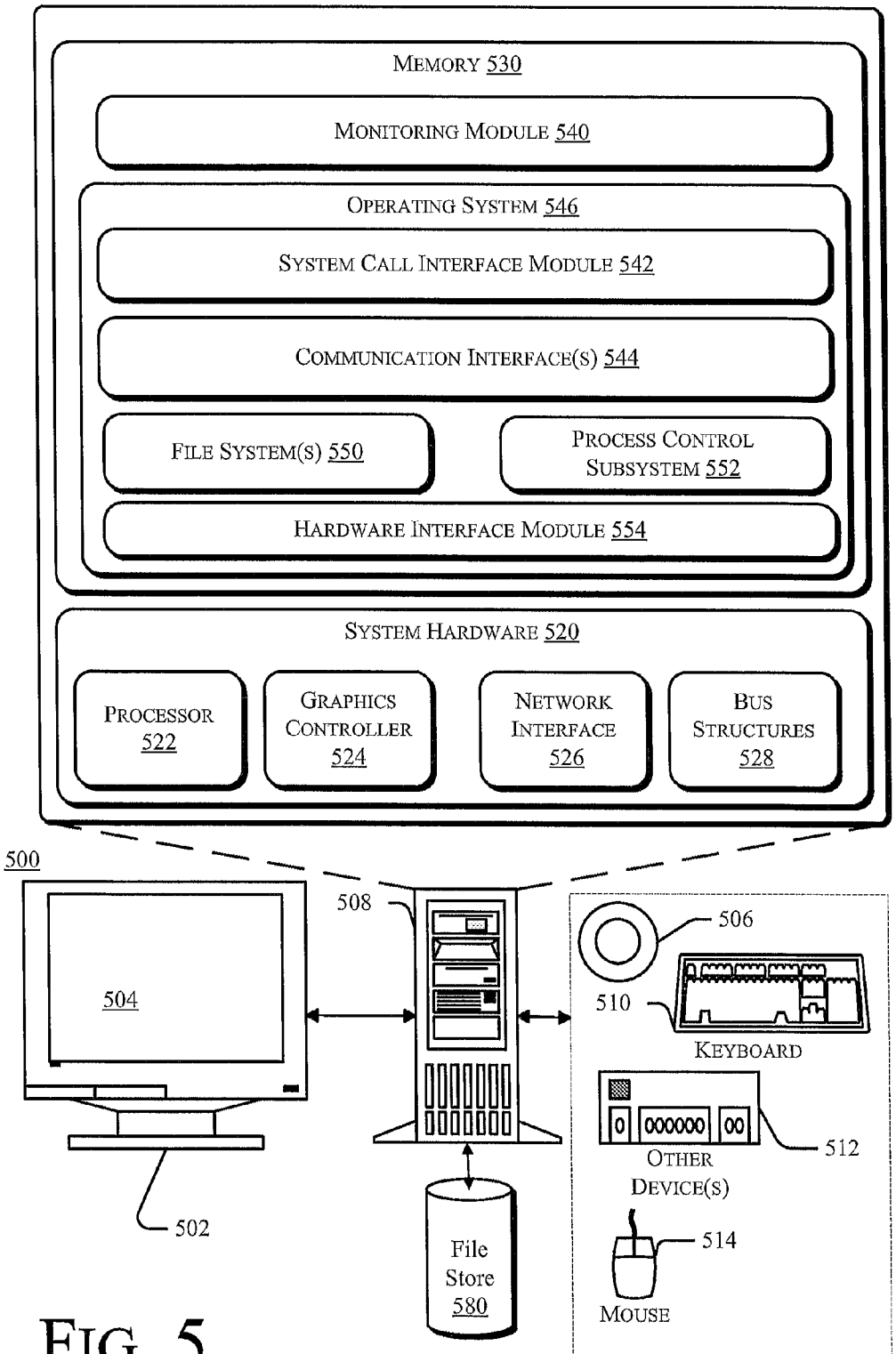
FIG. 5 a schematic illustration of a processing device, according to aspects.

As described above, position sensor(s) 140 and the gas sensor(s) 150 may be coupled to a processing device 160. In some embodiments the processing device 160 may be implemented as a general purpose computing system. FIG. 5 is a schematic illustration of a computing system 500 that may be used to monitor for airborne impurities. In some embodiments, system 500 includes a computing device 508 and one or more accompanying input/output devices including a display 502 having a screen 504, one or more speakers 506, a keyboard 510, one or more other I/O device(s) 512, and a mouse 514. The other I/O device(s) 512 may include a touch screen, a voice-activated input device, a track ball, and any other device that allows the system 500 to receive input from a user.

The computing device 508 includes system hardware 520 and memory 530, which may be implemented as random access memory and/or read-only memory. A file store 580 may be communicatively coupled to computing device 508. File store 580 may be internal to computing device 508 such as, e.g., one or more hard drives, CD-ROM drives, DVD-ROM drives, or other types of storage devices. File store 580 may also be external to computer 508 such as, e.g., one or more external hard drives, network attached storage, or a separate storage network.

System hardware 520 may include one or more processors 522, video controllers 524, network interfaces 526, and bus structures 528. In one embodiment, processor 522 may be embodied as an Intel® Pentium IV® processor available from Intel Corporation, Santa Clara, Calif., USA. As used herein, the term "processor" means any type of computational element, such as but not limited to, a microprocessor, a microcontroller, a complex instruction set computing (CISC) microprocessor, a reduced instruction set (RISC) microprocessor, a very long instruction word (VLIW) microprocessor, or any other type of processor or processing circuit.

Graphics controller 524 may function as an adjunction processor that manages graphics and/or video operations. Graphics controller 524 may be integrated onto the motherboard of computing system 500 or may be coupled via an expansion slot on the motherboard.

In one embodiment, network interface 526 could be a wired interface such as an Ethernet interface (see, e.g., Institute of Electrical and Electronics Engineers/IEEE 802.3-2002) or a wireless interface such as an IEEE 802.11a, b or g-compliant interface (see, e.g., IEEE Standard for IT-Telecommunications and information exchange between systems LAN/MAN—Part II: Wireless LAN Medium Access Control (MAC) and Physical Layer (PHY) specifications Amendment 4: Further Higher Data Rate Extension in the 2.4 GHz Band, 802.11G-2003). Another example of a wireless interface would be a general packet radio service (GPRS) interface (see, e.g., Guidelines on GPRS Handset Requirements, Global System for Mobile Communications/GSM Association, Ver. 3.0.1, December 2002).

Bus structures 528 connect various components of system hardware 528. In one embodiment, bus structures 528 may be one or more of several types of bus structure(s) including a memory bus, a peripheral bus or external bus, and/or a local bus using any variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

Memory 530 may include an operating system 546 for managing operations of computing device 508. In one embodiment, operating system 546 includes a hardware interface module 554 that provides an interface to system hardware 520. In addition, operating system 546 may include a file system 550 that manages files used in the operation of computing device 508 and a process control subsystem 552 that manages processes executing on processing device 160.

Operating system 546 may include (or manage) one or more communication interfaces 544 that may operate in conjunction with system hardware 520 to transceive data packets and/or data streams from a remote source. Operating system 546 may further include a system call interface module 542 that provides an interface between the operating system 546 and one or more application modules resident in memory 530. Operating system 546 may be embodied as a UNIX operating system or any derivative thereof (e.g., Linux, Solaris, etc.) or as a Windows® brand operating system, or other operating systems.

In one embodiment, memory 530 includes a monitoring module 540 to manage gas monitoring operations of the system 100. The monitoring module 540 may include logic instructions encoded in a computer-readable storage medium which, when executed by processor 522, cause the processor 522 to manage the system 100 to monitor gas components in chamber 110.

Figure 6:
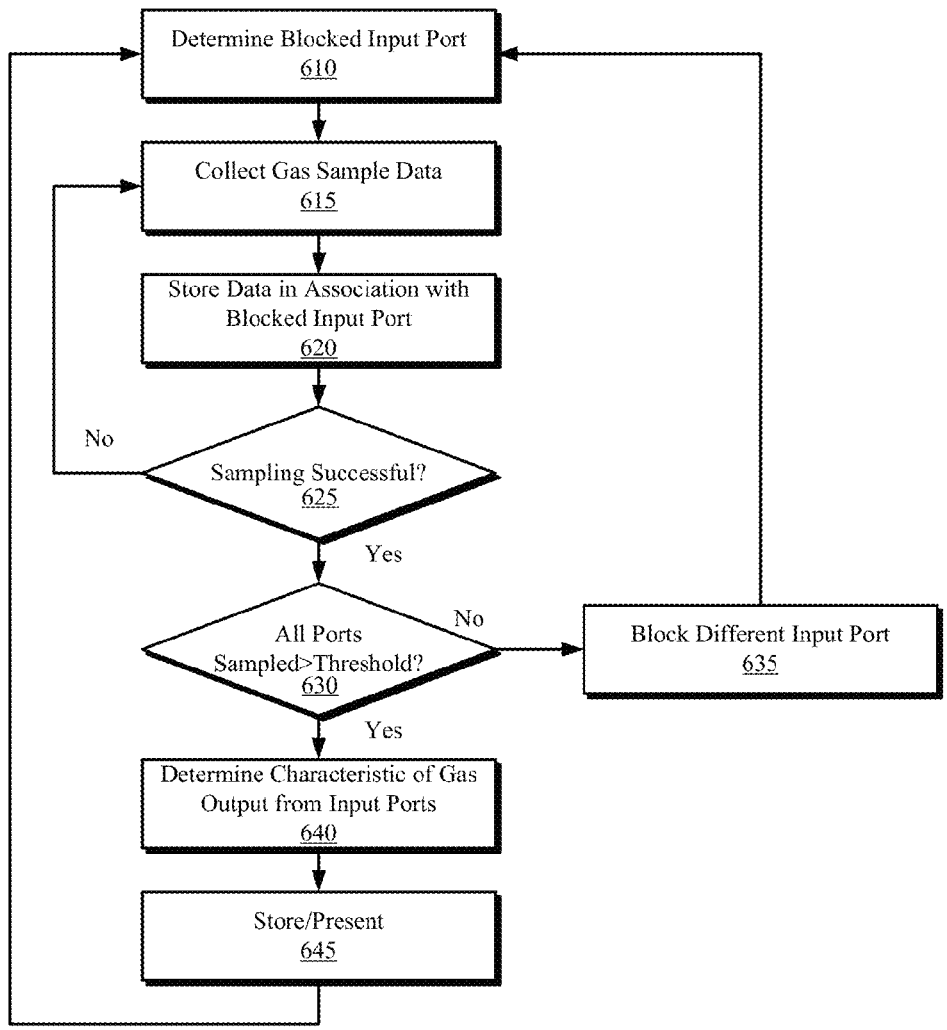
FIG. 6 is a flowchart illustrating operations in a gas sensing method, according to aspects.
Figure 7:
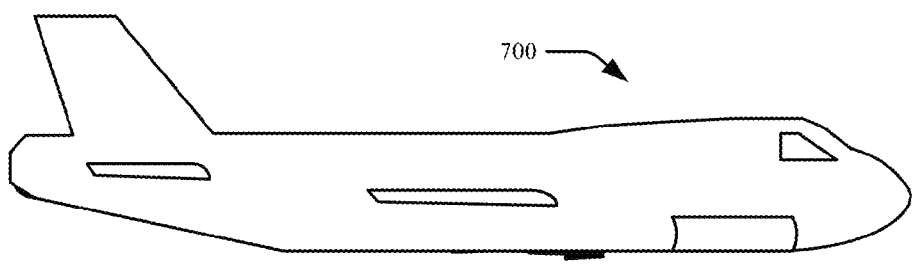
FIG. 7 is a schematic illustration of an aircraft, according to aspects.

FIG. 6 is a flowchart illustrating operations in a method detect airborne impurities, according to embodiments. Referring to FIG. 6, at operation 610 it is determined which input port 112 in chamber 110 is blocked. As described above, in some examples the position sensors 140 may generate signals which indicate which input port 112 in the chamber 110 is blocked. Alternatively, in the example depicted in FIG. 4 the processing device 160 controls the input ports 112 such that the processing device 160 is aware which input port 112 is closed.

At operation 615 gas sample data is obtained by a gas sensor 150. As described above, the gas sensor 150 may sense one or more attributes of a gas in the chamber 110. By way of example, if sensor 150 were an oxygen sensor then sensor 150 may detect a concentration of oxygen in the chamber 110. The processing device 160 may query the gas sensor 150 on a periodic basis, e.g., between about 100 milliseconds and 2000 milliseconds.

At operation 620 the gas sample data obtained in operation 615 is stored in association with an indicator of the input port 112 which was blocked while the sample data was collected. For example, the gas sample data may be stored in a data table or the like in memory 530 of processing device 160.

At operation 625 it is determined whether the sampling of the blocked port was successful. In some examples, the sampling may be considered successful if the blocked port is not open during sampling, e.g., due to movement of ball 116, and if the sampling duration continued for an adequate period of time. If, at operation 625, the sampling the blocked input port was not successful then control passes back to operation 615 and the sampling process continues. Thus, operations 615-625 define a loop pursuant to which processing device 160 may collect gas data samples from gas sensor 150.

By contrast, if at operation 625 the number of samples exceeds the threshold then control passes to operation 630. If, at operation 630 a threshold number of gas data samples have not been taken with all input ports 112 in the enclosure 110 blocked then control passes to operation 635 and a different input port is blocked. The threshold may be set as a predetermined number and may be static or dynamic. Further, the threshold may be a function of the number of input ports 112 in the chamber. In some examples the threshold may vary between about 12 samples and 100 samples. In the example chambers depicted in FIGS. 3-4 the processing device may have to wait for the ball 116 to be moved under the force of acceleration. By contrast, in the example depicted in FIG. 5 the processing device 160 may continue closing input ports 112 in a pseudo-random or ordered fashion until all input ports 112 have been closed.

By contrast, if at operation 630 a threshold number of gas data samples have been taken with all input ports 112 in the enclosure 110 blocked then control passes to operation 640 and the processing device 160 determines a characteristic of the gas from the respective input ports 112. In some examples, the processing device 160 may first determine an average of the gas sample data collected while each input port 112 was blocked. For example, if the processing device 160 is configured to collect 100 data samples for each blocked input port 112 then an average of the 100 data samples is determined. The total output ($I_t$) of the input ports may be determined by $$I_T = \frac{\sum_{i=1}^{n} H_i}{n-1} \quad \text{EQ (1)}$$

And the output of any given input port 112 may be determined by $$I_i = \frac{(2-n)\sum_{i=1}^{n} H_i}{n-1} \quad \text{EQ (2)}$$

Where:
$I_t$ is the total output from all input ports 112 combined
$I_i$ is a total output from a the $i^{th}$ input port;
n is a total number of input ports;
$H_i$ is average of measures taken while the $i^{th}$ input port is blocked.

Thus, the system 100 described herein enables gas sample data to be collected from chamber 110 while the input ports 112 are blocked in a pseudo-random fashion. The processing device 160 may then determine a characteristic (i.e. a composition) of the gas associated with any given input port 112. This output may be stored in a computer-readable medium such as memory 130 or presented on a user interface, thereby allowing a user to ascertain information about a single gas source 130 in a multi-source system, thereby eliminate the need for multiple expensive sensors and the power and weight requirements needed to support the sensors.

While various embodiments have been described, those skilled in the art will recognize modifications or variations which might be made without departing from the present disclosure. For example, while the processing device 160 is described as a fully functioning computer system, it will be recognized that the processing device 160 may be embodied as a specialized controller, e.g., an application specific integrated circuit (ASIC) or a field programmable gate array (FPGA).

In some embodiments a system 100 may be incorporated into compartments of on an aircraft 700, such as an airplane, helicopter, spacecraft or the like. In alternate embodiments a system 100 may be incorporated into a ground-based vehicle such as a truck, tank, train, or the like, or on a water-based vehicle such as a ship. In further embodiments a system 100 may be incorporated into a land-based device or system.

The examples illustrate the various embodiments and are not intended to limit the present disclosure. Therefore, the description and claims should be interpreted liberally with only such limitation as is necessary in view of the pertinent prior art.

What is claimed is:

1. A system to monitor outputs of a plurality of gas sources, the system comprising:
   a chamber comprising a plurality of input ports respectively positioned on a plurality of sloped surfaces, wherein the input ports are configured to receive a flow of gas from a plurality of gas sources;
   a ball that rolls over the plurality of sloped surfaces for repeatedly temporarily blocking one of the plurality of input ports;
   means for repeatedly detecting which particular input port of the plurality of input ports is blocked;
   means for repeatedly sampling data representative of the gas in the chamber; and
   means for repeatedly storing the data from the sensor in a memory in association with an indicator of the particular input port.

2. The system of claim 1, wherein the means for repeatedly detecting comprises a Hall effect position sensor.

3. The system of claim 1, wherein the means for repeatedly sampling comprises a gas sensor.

4. The system of claim 1, further comprising means to determine a characteristic of the gas in the chamber based on the data.

5. The system of claim 4, wherein the means to determine comprises a processor-based device comprising logic, at least partially including hardware logic, to compute:

$$I_i = \frac{(2-n)\sum_{i=1}^{n} H_i}{n-1}$$

where:
$I_i$ is a total output from an $i^{th}$ input port;
n is a total number of input ports; and
$H_i$ is average of measures taken while the $i^{th}$ input port is blocked.

6. A system to monitor outputs of a plurality of gas sources, the system comprising:
   a chamber comprising a plurality of input ports positioned in respective discrete sections that are partially divided from each by a plurality of structures, wherein the input ports are configured to receive a flow of gas from a plurality of gas sources;

a ball that repeatedly rolls into one of the discrete sections for temporarily blocking one of the plurality of input ports;
means for repeatedly detecting which particular input port of the plurality of input ports is blocked;
means for repeatedly sampling data representative of the gas in the chamber; and
means for repeatedly storing the data from the sensor in a memory in association with an indicator of the particular input port.

7. An aircraft comprising:
a system to monitor outputs of a plurality of gas sources on the aircraft, the system comprising:
　a chamber comprising a plurality of input ports respectively positioned on a plurality of sloped surfaces, wherein the input ports are configured to receive gas from the plurality of gas sources;
　a ball that rolls over the plurality of sloped surfaces for repeatedly temporarily blocking one of the plurality of input ports;
　means for repeatedly detecting which particular input port of the plurality of input ports is blocked;
　means for repeatedly sampling data representative of the gas in the chamber; and
　means for repeatedly storing the data from the sensor in a memory in association with an indicator of the particular input port.

8. The aircraft of claim 7, wherein the means for repeatedly detecting comprises a Hall effect position sensor.

9. The aircraft of claim 7, wherein the means for repeatedly sampling comprises a gas sensor to collect gas samples from the chamber.

10. The aircraft of claim 7, further comprising means to determine a characteristic of the gas in the chamber based on the data.

11. The aircraft of claim 10, wherein the means to determine comprises a processor-based device comprising logic, at least partially including hardware logic, to compute:

$$I_i = \frac{(2-n)\sum_{i=1}^{n} H_i}{n-1}$$

where:
　$I_i$ is a total output from an $i^{th}$ input port;
　n is a total number of input ports; and
　$H_i$ is average of measures taken while the $i^{th}$ input port is blocked.

12. An aircraft comprising:
a system to monitor outputs of a plurality of gas sources, the system comprising:
　a chamber comprising a plurality of input ports positioned in respective discrete sections of the chamber, wherein the discrete sections are partially divided from each other by a plurality of structures, and wherein the input ports are configured to receive a flow of gas from the plurality of gas sources;
　a ball that repeatedly rolls into one of the discrete sections for temporarily blocking one of the plurality of input ports;
　means for repeatedly detecting which particular input port of the plurality of input ports is blocked;
　means for repeatedly sampling data representative of the gas in the chamber; and
　means for repeatedly storing the data from the sensor in a memory in association with an indicator of the particular input port.

13. A method to monitor outputs of a plurality of gas sources, the method comprising:
　receiving inputs from the plurality of gas sources in a plurality of input ports in a chamber, wherein the chamber comprises a plurality of discrete sections that are partially divided from each other by a plurality of structures with the input ports respectively positioned in the plurality of discrete sections;
　repeatedly temporarily blocking one of the plurality of input ports by moving a ball that rolls into one of the discrete sections;
　repeatedly detecting which particular input port of the plurality of input ports is blocked;
　repeatedly sampling, from a sensor, data representative of the gas in the chamber; and
　repeatedly storing the data from the sensor in a memory in association with an indicator of the particular input port.

14. The method of claim 13, further comprising determining a characteristic of the gas in the chamber based on the data.

15. The method of claim 14, wherein determining an output from the one of the plurality of input ports from the data comprises computing:

$$I_i = \frac{(2-n)\sum_{i=1}^{n} H_i}{n-1}$$

where:
　$I_i$ is a total output from an $i^{th}$ input port;
　n is a total number of input ports; and
　$H_i$ is average of measures taken while the $i^{th}$ input port is blocked.

16. A method to monitor outputs of a plurality of gas sources, the method comprising:
　receiving inputs from the plurality of gas sources in a plurality of input ports in a chamber, wherein the chamber comprises a plurality of sloped surfaces and the input ports are respectively positioned on the plurality of sloped surfaces;
　repeatedly temporarily blocking one of the plurality of input ports by moving a ball that rolls onto one of the sloped surfaces;
　repeatedly detecting which particular input port of the plurality of input ports is blocked;
　repeatedly sampling, from a sensor, data representative of the gas in the chamber; and
　repeatedly storing the data from the sensor in a memory in association with an indicator of the particular input port.

* * * * *